United States Patent [19]
Balthasart et al.

[11] Patent Number: 5,626,725
[45] Date of Patent: May 6, 1997

[54] PROCESS FOR SEPARATION OF 1,1-DIFLUOROETHANE FROM ITS MIXTURE WITH HYDROGEN FLUORIDE

[75] Inventors: Dominique Balthasart, Brussels; Philippe Decap, Woluwe-St-Pierre, both of Belgium

[73] Assignee: Solvay (Société Anonyme), Brussels, Belgium

[21] Appl. No.: 419,557

[22] Filed: Apr. 10, 1995

[30] Foreign Application Priority Data

Apr. 11, 1994 [FR] France ................................ 94 04354

[51] Int. Cl.$^6$ ................................................. B01D 3/10
[52] U.S. Cl. ................................ 203/91; 203/80; 570/178
[58] Field of Search ........................... 203/80, 91; 570/178

[56] References Cited

U.S. PATENT DOCUMENTS 4,021,312  5/1977  Carter .......................... 203/80

FOREIGN PATENT DOCUMENTS 6293675  10/1994  Japan .......................... 570/178

OTHER PUBLICATIONS

Abstract of Soviet Union Patent No. 341788, 1972.

Yang et al: "Preparation, separation and purification of 1,1-difluoroethane", Chemical Abstracts, vol. 119, No. 11, Sep. 13, 1993, Colombus, Ohio, US, abstract No. 116776 & CN-A-1069019, Feb. 17, 1993.

Primary Examiner—Robert J. Warden
Assistant Examiner—Theresa T. Snider
Attorney, Agent, or Firm—Spencer & Frank

[57] ABSTRACT

The invention relates to a process for separating 1,1-difluoroethane from its mixtures with hydrogen fluoride, in which the mixture is subjected to a distillation in a column operating at a pressure of less than 10 bar.

5 Claims, 3 Drawing Sheets

PROCESS FOR SEPARATION OF 1,1-DIFLUOROETHANE FROM ITS MIXTURE WITH HYDROGEN FLUORIDE

FIELD OF THE INVENTION

The invention relates to a process for separating 1,1-difluoroethane from its mixtures with hydrogen fluoride.

TECHNOLOGY REVIEW

It is known to prepare 1,1-difluoroethane (HFA-152a) by reaction of hydrogen fluoride (HF) with a chlorinated compound containing two carbon atoms, such as vinyl chloride, 1-chloro-1-fluoroethane or 1,1-dichloroethane.

The HFA-152a required is generally obtained as a mixture with unconverted reactants and hydrogen chloride (HCl). The separation of HCl from the other constituents of the mixture of reaction products is easily carried out by distillation in a column at elevated pressure, of the order of 12 bar or more. The HCl is taken off at the top of the column and the other constituents of the mixture of reaction products are recovered at the bottom of the column. The HFA-152a must then be separated from the other constituents of the mixture of the reaction products. It has been observed, however, that it is impossible to separate HFA-152a and HF completely by distillation in a column operating at a pressure of the order of 10 bar or more because, in these conditions, these compounds form an azeotrope with a minimum boiling temperature. It is certainly possible to absorb in water the HF present in the HF/HFA-152a azeotropic mixture. However, since the process of manufacture of HFA-152a requires HF to be introduced in anhydrous form, HF absorbed in water cannot be recycled as it is to the synthesis reactor, and this constitutes a disadvantage.

The subject of the invention is a simple process for separation of HFA-152a from its azeotropic mixtures with HF, which makes it possible at the same time to obtain HFA-152a in a substantially pure form and to recover HF in anhydrous form.

SUMMARY OF THE INVENTION

The invention consequently relates to a process for separation of 1,1-difluoroethane from a mixture of 1,1-difluoroethane and hydrogen fluoride, obtained at a pressure higher than 10 bar, in which the mixture is subjected to a distillation in a column operating at a pressure of less than 10 bar.

DETAILED DESCRIPTION OF THE INVENTION

The distillation column intended to separate 1,1-difluoroethane from its mixtures with hydrogen fluoride preferably operates at a pressure lower than or equal to 5 bar. A very good separation is obtained when the distillation is performed at a pressure lower than or equal to 2 bar.

In fact, the HFA-152a/HF azeotrope, the existence of which has been detected at pressures higher than or equal to 10 bar, disappears when the pressure is reduced below 10 bar.

The composition of the azeotropic mixtures of HFA-152a and HF at different temperatures and pressures is the following:

| Pressure (bar) | Temperature (°C.) | HFA-152a (molar fraction) | HF (molar fraction) |
| --- | --- | --- | --- |
| 23.5 | 80 | 0.97 | 0.03 |
| 15.1 | 60 | 0.99 | 0.01 |
| 8.9 | 40 | no azeotrope | |
| 5.2 | 20 | no azeotrope | |

The invention makes use of the disappearance of the azeotrope between HFA-152a and HF at reduced pressure, in order to separate HFA-152a from its mixtures with HF. Such a separation is obtained by subjecting the mixture to a distillation in a column operating at a pressure of less than 10 bar (and at an associated temperature of less than 43° C.). In these conditions HFA-152a which contains a quantity of HF that is smaller than that of the azeotropic composition existing at higher pressure is recovered at the top of the distillation column, and HF in anhydrous form, substantially free from HFA-152a, is recovered at the bottom of the distillation column. By performing the distillation at a pressure of less than 2 bar, HFA-152a substantially free from any HF is successfully obtained at the top of the distillation column.

The process according to the invention applies particularly to the separation of HFA-152a from its mixtures with unconverted HF during the manufacture of HFA-152a by hydrofluorination of vinyl chloride and/or of 1,1-dichloroethane at a pressure higher than 10 bar. In such a process the mixture of reaction products leaving the hydrofluorination reactor contains, in addition to HFA-152a and unconverted HF, vinyl chloride and/or 1,1-dichloroethane, hydrogen chloride (HCl) originating from the removal of the chlorine from the starting compound and optionally inert diluents and various by-products such as 1-chloro-1-fluoroethane (HFA-151a), in small quantity.

Figure 1:
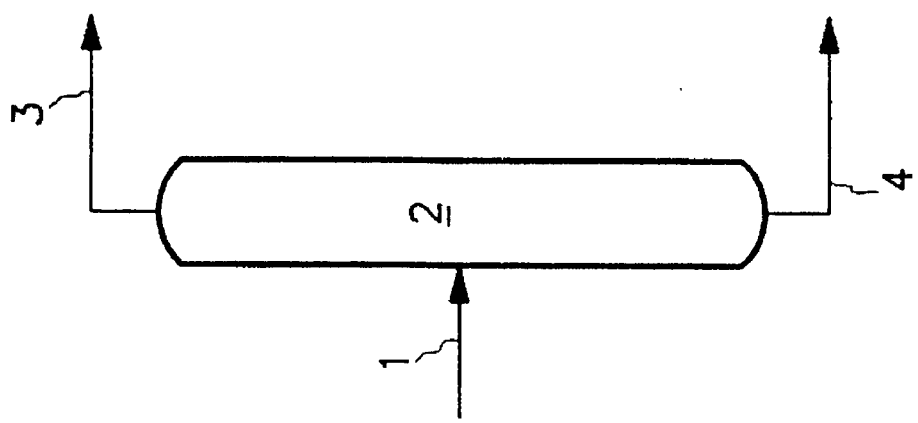
FIG. 1 illustrates a process according to the invention applied directly to a mixture of products originating from a reactor. In this embodiment the mixture of reaction products is introduced via a conduit (1) into a distillation column (2). The effluent (3) is taken off at the top column (2).
Figure 2:
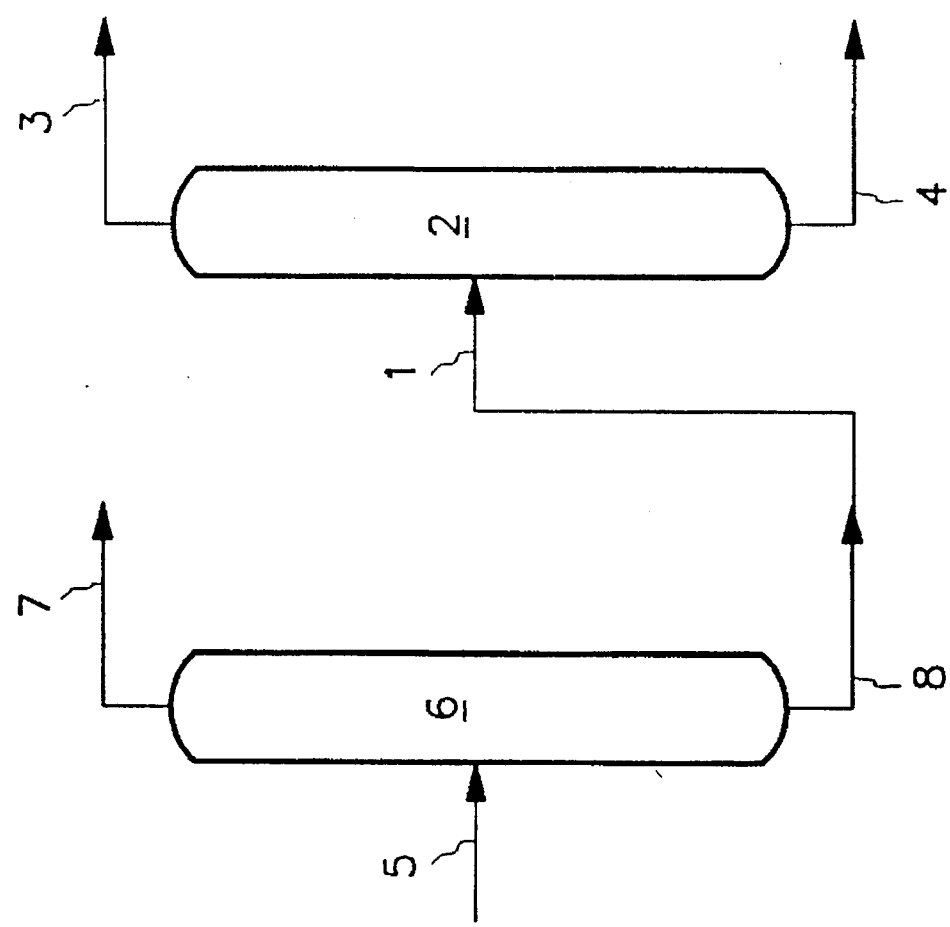
FIG. 2 illustrates an alternative form of the process according to the present invention. In this alternative the mixture of reaction products from a reactor is introduced via a conduit (5) into a distillation column for light materials (6), from the top of which HCl is taken off at (7). The other components of the mixture are recovered at the bottom (8) of the distillation column for light materials (6) and are introduced via conduit (1) into the distillation column (2). The effluent (3) is taken off at the top column (2). The remaining reaction products are recovered at the bottom (4) of the column (2).
Figure 3:
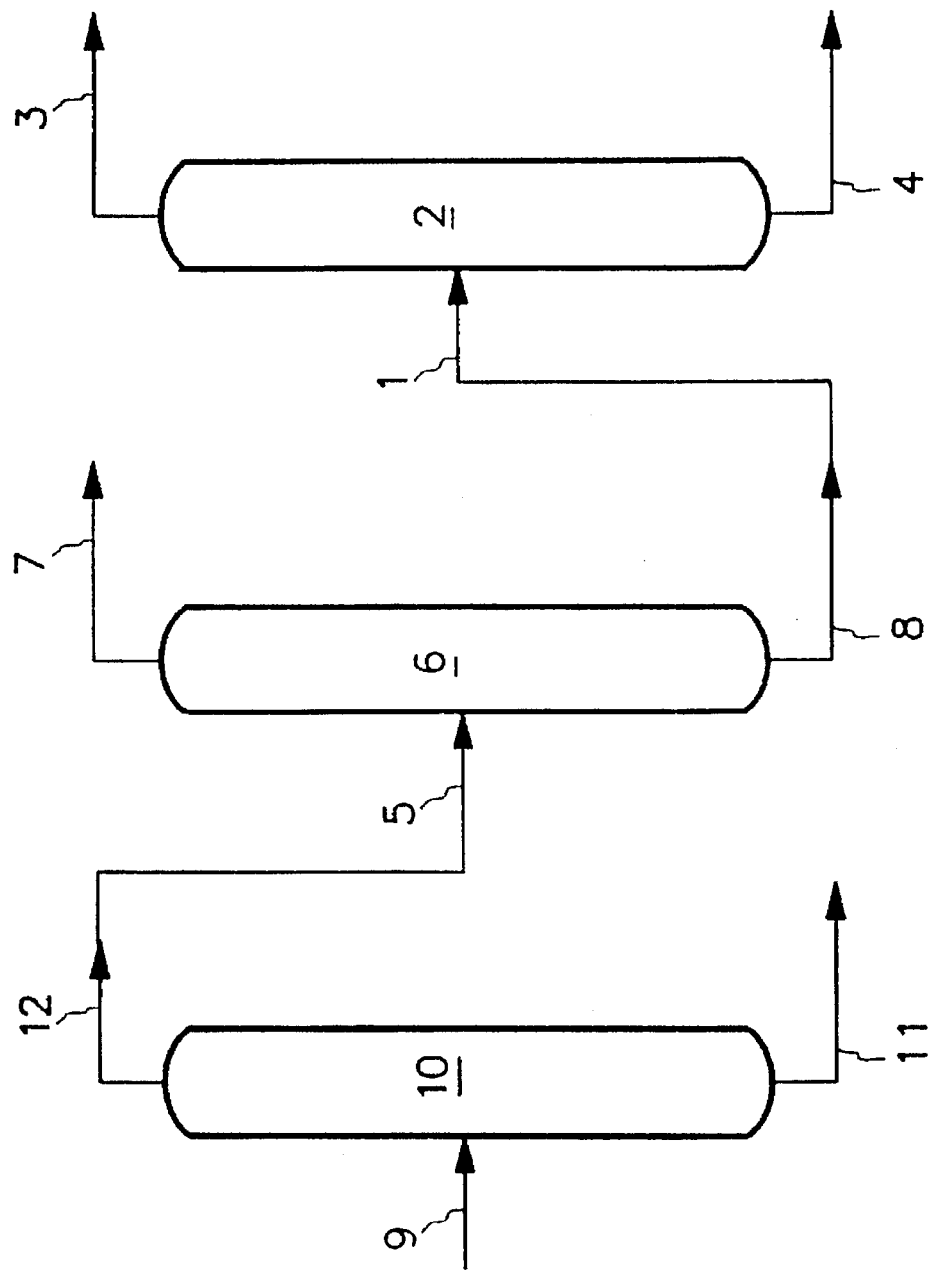
FIG. 3 illustrates a third alternative of the process according to the invention. A mixture of reaction products from a reactor is first introduced via a conduit (9) into a distillation column for heavy materials (10). Part of the reaction products are recovered at (11) at the bottom of column (10). An effluent is taken off at (12) at the top of column (10). This effluent is introduced via conduit (5) into the distillation column (6). HCl is taken off at (7) at the head of column (6). The other components of the mixture are recovered at the bottom (8) of the column (6) and are introduced via conduit (1) into the distillation column (2). The effluent (3) is drawn off at the top of column (2). HF is recovered at the bottom (4) of the column (2).

The invention will be understood better when reference is made to the diagrams shown in FIGS. 1 to 3, which show three distillation plants applied to the treatment of a mixture of reaction products originating from a reactor for hydrofluorination of vinyl chloride. In these figures the same reference marks denote identical components.

In a first alternative form, shown diagrammatically in FIG. 1, the process according to the invention is applied directly to a mixture of reaction products originating from a reactor for hydrofluorination of vinyl chloride, such a mixture usually including HFA-152a product, HCl by-product, unchanged HF and vinyl chloride and HFA-151a and 1,1-dichloroethane. In this alternative form the mixture of the reaction products is introduced via a conduit (1) into a distillation column (2) operating at a pressure lower than 10 bar. The effluent (3) taken off at the top of the column (2) contains HFA-152a and HCl. HF, vinyl chloride, HFA-151a and 1,1-dichloroethane, which can be recycled to the reactor for hydrofluorination of vinyl chloride, are recovered at the bottom (4) of the column (2). The HFA-152a in the gaseous effluent (3) can subsequently be separated conventionally from HCl by distillation.

In a second alternative form, shown diagrammatically in FIG. 2, HCl is first of all separated from the mixture of reaction products. This alternative form is conventionally implemented by introducing the mixture of reaction products from the hydrofluorination reactor via a conduit (5) into a distillation column for light materials (6), operating at a pressure of more than 10 bar, from the top of which HCl is taken off at (7). The other components of the mixture are recovered at the bottom (8) of the distillation column for light materials (6) and are introduced via conduit (1) into the distillation column (2) operating, in accordance with the invention, at a pressure lower than 10 bar. The effluent (3) taken off at the top of the column (2) contains HFA-152a. HF, vinyl chloride, HFA-151a and 1,1-dichloroethane, which may be recycled to the hydrofluorination reactor, are recovered at the bottom (4) of the column (2).

In a third alternative form of the process, shown diagrammatically in FIG. 3, the mixture of reaction products from the hydrofluorination reactor is first of all introduced via a conduit (9) into a distillation column for heavy materials (10), operating at a pressure of more than 10 bar. Part of the HF, vinyl chloride, HFA-151a and 1,1-dichloroethane, which may be recycled to the hydrofluorination reactor, are recovered at the bottom of the column (10), at (11). An effluent containing HFA-152a and HF in proportions of the azeotropic composition at the operating pressure of the column (10) is taken off at the top of the column (10), at (12), together with HCl. This effluent is introduced via conduit (5) into the distillation column for light materials (6), also operating at a pressure higher than 10 bar. HCl is taken off at the head of the column (6), at (7). The other components of the mixture are recovered at the bottom (8) of the column (6) and are introduced via conduit (1) into the distillation column (2) operating, in accordance with the invention, at a pressure lower than 10 bar. The effluent (3) drawn off at the top of the column (2) contains HFA-152a. HF, which may be recycled to the hydrofluorination reactor, is recovered at the bottom (4) of the column (2).

The third alternative form of the process according to the invention appears to be particularly advantageous when HFA-152a is prepared from vinyl chloride and/or 1,1-dichloroethane in a hydrofluorination reactor operating at elevated pressure, of the order of 15 to 30 bar, in boiling liquid phase. In this case the column (10) may advantageously comprise only a top section mounted above the hydrofluorination reactor used as boiler.

EXAMPLES

The following examples illustrate the invention without any limitation being implied.

EXAMPLE 1

A mixture containing 57 mol % of HF and 43 mol % of HFA-152a was introduced into a distillation column comprising 7 theoretical plates, at a total pressure of 8 bar. The product obtained at the top of the column contained 1.8 mol % of HF and 98.2 mol % of HFA-152a.

EXAMPLE 2

Under the same conditions as those of Example 1, at a total pressure of 2 bar, the product obtained at the top of the column under total reflux contained 0.5 mol % of HF and 99.5 mol % of HFA-152a.

EXAMPLE 3

A mixture containing 1.2 mol % of HF and 98.8 mol % of HFA-152a was introduced into the distillation column of Example 1 at a total pressure of 2 bar. The product obtained at the top of the column contained 0.2 mol % of HF and 99.8 mol % of HFA-152a.

What is claimed is:

1. A process for the manufacture of 1,1-difluoroethane comprising:

(a) reacting, at a pressure higher than 10 bar, hydrogen fluoride with a chlorinated compound selected from vinyl chloride and 1,1-dichloroethane, to obtain a mixture of reaction products containing 1,1-difluoroethane, hydrogen chloride and unconverted hydrogen fluoride;

(b) distilling said mixture in a column having a top operating at a pressure of 10 bar or less; and (c) recovering, at the top of said column, a purified stream of 1,1-difluoroethane, said stream containing less than 1 mol % of hydrogen fluoride.

2. The process according to claim 1, wherein the operating pressure of the column is lower than or equal to 5 bar.

3. The process according to claim 1, wherein the operating pressure of the column is lower than or equal to 2 bar.

4. The process according to claim 1, wherein hydrogen chloride generated during the hydrofluorination is removed from the mixture before the mixture is subjected to distillation.

5. The process according to claim 1, wherein hydrogen fluoride is recovered in anhydrous form.

* * * * *